(12) United States Patent
Duic

(10) Patent No.: US 7,541,191 B2
(45) Date of Patent: Jun. 2, 2009

(54) INTEGRATED APPARATUS FOR HEMATOLOGICAL ANALYSIS AND RELATED METHOD

(75) Inventor: Giovanni Battista Duic, Cassacco (IT)

(73) Assignee: Sire Analytical Systems SRL, Udine (IT)

( * ) Notice: Subject to any disclaimer, the term of this patent is extended or adjusted under 35 U.S.C. 154(b) by 164 days.

(21) Appl. No.: 10/570,527

(22) PCT Filed: Sep. 1, 2004

(86) PCT No.: PCT/IB2004/002824

§ 371 (c)(1),
(2), (4) Date: Mar. 3, 2006

(87) PCT Pub. No.: WO2005/022125

PCT Pub. Date: Mar. 10, 2005

(65) Prior Publication Data

US 2006/0288760 A1   Dec. 28, 2006

(30) Foreign Application Priority Data

Sep. 3, 2003   (IT) .......................... UD2003A0174

(51) Int. Cl.
G01N 33/49 (2006.01)
G01N 33/86 (2006.01)

(52) U.S. Cl. ................ 436/70; 73/61.62; 73/61.65; 422/68.1; 422/73; 436/164

(58) Field of Classification Search ............... 73/61.69, 73/61.62, 61.65; 422/68.1, 73, 82.05; 436/70, 436/164

See application file for complete search history.

(56) References Cited

U.S. PATENT DOCUMENTS

| 3,192,969 | A |   | 7/1965 | Baruch et al. |
| 5,827,746 | A | * | 10/1998 | Duic ........................... 436/70 |
| 6,336,358 | B1 | * | 1/2002 | Kishimori et al. .......... 73/61.65 |
| 6,632,679 | B1 | * | 10/2003 | Breda .......................... 436/70 |
| 2004/0065143 | A1 | * | 4/2004 | Husher ...................... 73/64.53 |

FOREIGN PATENT DOCUMENTS

| EP | 0 732 576 | 9/1996 |
| EP | 1 098 188 | 5/2001 |
| WO | WO 95/14224 | 5/1995 |

OTHER PUBLICATIONS

Piva et al. "Determination of the length of sedimentation reaction in non-anticoagulated blood with the microtest 1". *Clin Chem Lab Med*, vol. 40, No. 7, pp. 713-717 (2002).

* cited by examiner

Primary Examiner—David A. Rogers
(74) Attorney, Agent, or Firm—Hamre, Schumann, Mueller & Larson, P.C.

(57) ABSTRACT

Integrated apparatus and method for hematological analyses, wherein the apparatus comprises, arranged substantially in line and integrated substantially in a single machine, a device (14) of the optical type to detect substantially instantaneously the speed of blood sedimentation (ESR) by measuring the optical density, or absorbance, of the blood sample, and a measuring assembly (18) with a cell-counter function or suchlike.

8 Claims, 1 Drawing Sheet

INTEGRATED APPARATUS FOR HEMATOLOGICAL ANALYSIS AND RELATED METHOD

FIELD OF THE INVENTION

The present invention concerns an integrated apparatus to perform hematological analyses on blood samples. To be more exact, the invention concerns an apparatus that integrates in the same machine at least a cell-counter function, or other type of analysis connected with a cell-counter function, and the function of detecting the speed of blood sedimentation, or ESR.

The invention also concerns the method performed by such apparatus.

BACKGROUND OF THE INVENTION

In the field of medical analyses, pathological states, defined as inflammatory, are ascertained by measuring also the speed of sedimentation of the corpuscular part of the blood (ESR).

Known methods to measure ESR are generally characterized by long analysis times (from 30 to 60 minutes), which prevent such analysis being performed in succession with other, faster analyses, for example cell-counter analyses.

Moreover, known methods generally have to use throw-away containers, which entails an increase in costs both for purchasing them and for their disposal. Furthermore, a great quantity of blood is needed to perform the analysis, normally from 1 to 3 ml, and this entails problems in particular cases, for example when the analysis is to be made on children.

A method to detect the ESR is known, proposed by the same Applicant in EP-A-1.098.188, which provides to take a sample of blood to be analyzed, not diluted and to which no anti-coagulants or other substances have been added, from a container in which it is preserved, and to introduce this sample into a capillary tube, which is used for various measurements made on different samples.

This method is based on detecting the optical density or absorbance of the blood at a point of the measurement volume, by instantaneously stopping the flow of blood inside the capillary, in which a photometric signal correlated to the ESR examination is detected, according to the reference method known as Westergren (see for example the article "Determination of the Length of Sedimentation Reaction.." by Piva E., Fassina P. and Plebani M., published in Clin. Chem. Lab. Med. 2002; 40(7); pages 713-717)

The study of absorbance over time allows to work out the ERS value by eliminating the initial dead times, and thus considerably reducing the overall times needed, and obviating the need to use throw-away containers for the analysis. Moreover, the necessary quantity of blood to be analyzed is smaller and hence the analysis can be carried out without difficulty even on pediatric patients.

Another known method for determining the speed of sedimentation of blood is described in EP-A-0.732.576, also in the name of the present Applicant. Here too, the method uses the detection of the optical density, or absorbance, of a blood sample at a point of the measurement volume while said sample is subjected to centrifugal rotation inside a capillary tube.

The study of the absorbance in the blood sample subjected to analysis allows to find other parameters too, correlated to the speed of sedimentation, such as viscosity, elasticity or density, as indicated particularly in EP'188.

Moreover, the characteristics and peculiarities of the analysis made in this way, particularly the use of a blood sample in movement inside a tube, the non-use of throw-away containers and the extremely rapid response times, have led the present Applicant to hypothesize that it can be integrated, in line and with sequential measurements, with other types of hematological analyses, such as for example the analysis made by cell-counters.

Cell-counters are a category of measuring instruments used in clinical analysis laboratories which provide the fundamental parameters of hematology, such as counting red corpuscles, white corpuscles, platelets, hematocrit, and other parameters concerning the form and size of the corpuscle part of the blood. In order to perform this analysis, the machine uses a so-called primary blood sample, taken from the patient and collected in a sealed container which has a top that can be perforated by a needle in order to pick up the sample to be analyzed.

It must be considered that, in diagnostic techniques, the analysis performed by the cell-counters has always been considered not compatible time-wise with what is connected to measuring ESR, and hence also with reference to the parameters of viscosity, elasticity, density or similar, which can be obtained from the study of absorbance as proposed in EP'188 and EP'576.

In fact, in the state of the art, and before the method to measure ESR as described in EP'188 was developed, the producers of cell-count machines had never thought of integrating such machines and the devices used to measure the speed of blood sedimentation into a single apparatus, because of the intrinsic obstacles and incompatibilities as pointed out above.

It should also be noted that the usual and traditional techniques for measuring ESR use diluted blood, mixed with anti-coagulants which are not compatible with subsequent analyses such as those concerning the cell-count, whereas the technique described in EP'188 uses a dry state anti-coagulant (EDTA) which is the same as that used in primary test tubes used for cell-count analyses.

Document WO-A-95/14224 describes an apparatus that uses the measurement obtained by a cell-counter in order to find, empirically and by means of calculations, the ESR value. To be more exact, the apparatus provides a first analysis section wherein a blood sample is sent to a measuring cell provided with four electrodes, inside which the electric impedance of the blood sample is measured.

In a second analysis section another blood sample is subjected, possibly after being suitably mixed with a diluting product, to a step to determine the hematocrit. It is necessary to use another blood sample in an apparatus of this type since the measurement of the impedance, performed in the first analysis section, alters the sample irreversibly, which cannot therefore be used in sequence and in line to perform the measurement of the hematocrit too.

The data relating to the impedance of the blood and its hematocrit, plus the value of the temperature relating to the impedance measuring cell as measured by a suitable measuring element, are sent to a processing unit that calculates empirically, from these data, the ESR value.

The limits and disadvantages of an apparatus of this type are first of all its complexity and the large number of components it requires, both to detect the parameters and also to calculate and process the data.

Above all, however, the result obtained does not guarantee reliability and precision, on the one hand because intrinsically the empirical calculation process does not allow to ensure that precise values are obtained, and on the other hand because it adds together errors of tolerance due to no fewer than three different measuring systems.

It must in any case be considered that, in substance, this known apparatus does not perform an analytical and reliable measurement, in line, in sequence, and with the same blood sample, both of the speed of blood sedimentation and also of the hematocrit.

The purpose of the invention is therefore to achieve a device and propose a relative method to perform hematological analyses which integrates, in a single apparatus—small, compact and easy to transport—the functions of measuring, in line, in close sequence and with the same blood sample, the speed of blood sedimentation (ESR) in a machine able to perform at least the cell-count function and/or other connected analyses.

The Applicant has devised and embodied the present invention in order to obtain this purpose and other advantages as shown hereafter.

SUMMARY OF THE INVENTION

The present invention is set forth and characterized in the respective main claims, while the dependent claims describe other characteristics of the present invention.

The integrated apparatus according to the present invention comprises at least a collection element for one or more suitably sealed containers; each container is equipped with a relative top suitable to be perforated by means of at least a pick-up needle, in order to pick up the sample to be analyzed, in a quantity of between 30 and 200 µl.

The sealed container is a so-called "primary test tube" normally used in cell-count machines, wherein the blood remains in a state of rest, and only a dry state anti-coagulant of the EDTA type is added, and it is not further diluted or mixed with other liquid or solid substances.

This sample is sent, by means of pump means and through a circulation circuit, inside a capillary tube cooperating with an optical system suitable to emit electromagnetic radiations in the field of 100-1500 nm, advantageously 200-1000 nm, and to detect the radiation transmitted through the sample after having interrupted the flow of blood instantaneously, according to the teaching of EP'188. From this transmitted radiation, the ESR value is obtained by studying the optical density, or absorbance, of the blood sample as described for example in EP'576.

Since this analysis is performed in line, since it is not destructive and does not change in any way the initial chemical-physical characteristics of the blood sample—quite the contrary, for example, of a measurement of impedance—the same sample can then be sent, substantially without any break in continuity, and in a very close sequence, inside the measuring assembly of the cell-counter in order to perform the processes connected with such measurement.

After the measurements made by the cell-counter, the blood sample is discharged into a discharge container.

According to a variant, at least some of the measuring components of the cell-counters are located upstream of the device to measure the ESR.

With this system, therefore, the same device, of the type with a pick-up needle, and the same system with a pump that feeds the blood sample, can be shared both by the device that measures the ESR and also by the one that functions as a cell-counter.

The two measuring devices can therefore be arranged in series together, at a close distance from each other, and the whole thing can be housed inside a small container, compact, transportable and easily located inside a laboratory or a hospital surgery.

According to a variant, a single pick-up needle is connected to two paths that divide, one passing through the optical system to measure the ESR and the other through the cell-counter measuring systems or suchlike.

According to another, although less advantageous variant, two pick-up needles are used to pick up the respective samples to be sent to the relative measuring systems.

The two measuring systems are commanded and governed by the same command and control unit which selectively activates and coordinates the functioning thereof; the command and control unit is associated in known manner with interfaces that connect and communicate with the outside, such as a monitor, a keyboard to forward commands and to insert data and parameters, and possibly a printer to print out the values resulting from the analyses. According to a variant, the measuring system is connected on line for the automatic exchange of information between remote users.

In one embodiment of the invention, the pump means are reversible and allow to invert the flow inside the circuit; it is thus possible to re-homogenize the blood sample and rapidly repeat measurements thereon.

The capillary is also able to be thermostated in order to allow analysis to be carried out at a constant temperature, which can be pre-set as desired.

BRIEF DESCRIPTION OF THE DRAWING

These and other characteristics of the present invention will become clear from the following description of a preferential form of embodiment, given as a non-restrictive example, with reference to FIG. 1, which is a schematic view of an integrated apparatus for hematological analyses according to the invention.

DETAILED DESCRIPTION OF A PREFERENTIAL EMBODIMENT

Figure 1:
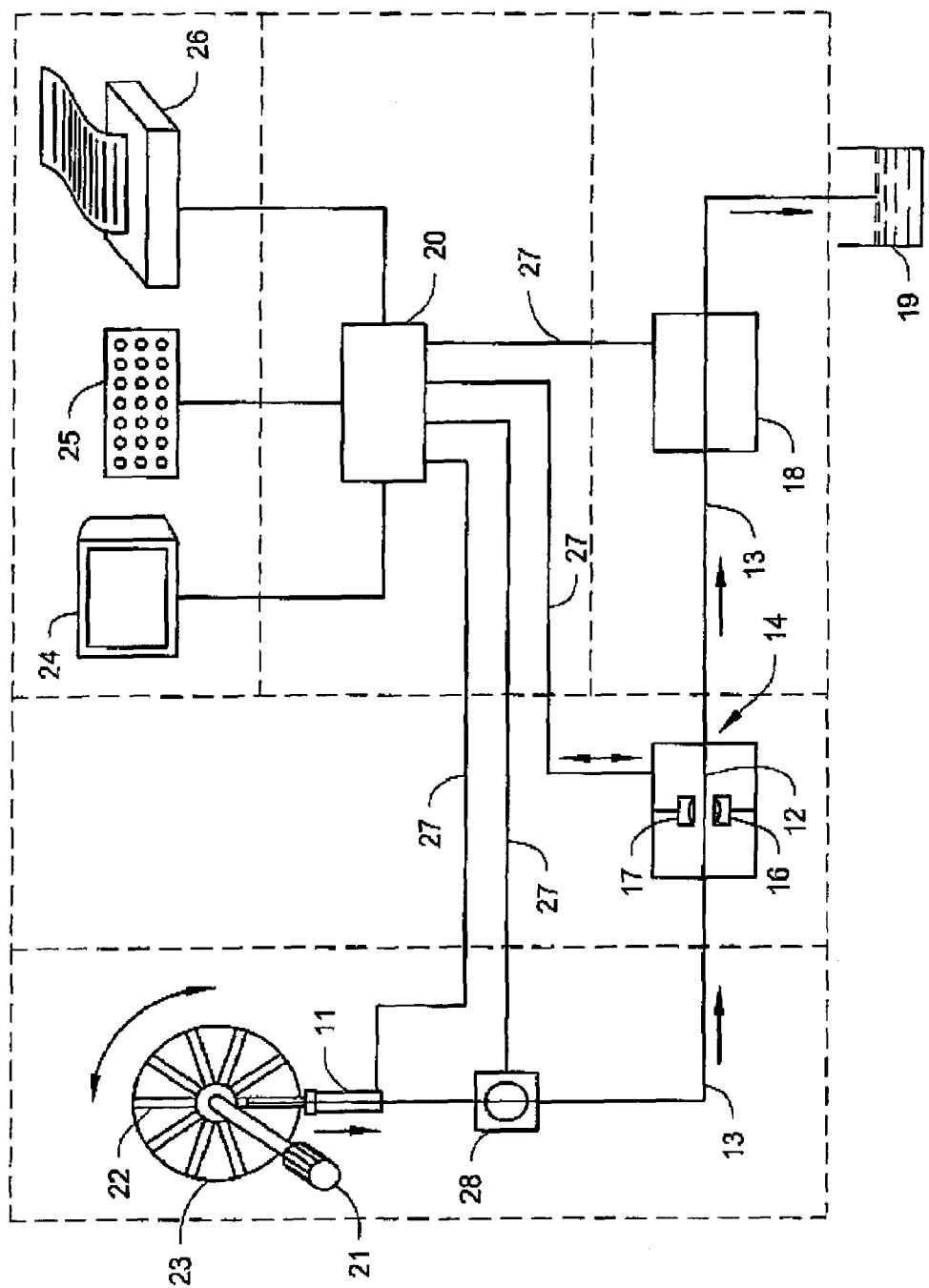

FIG. 1 shows a schematic view of an apparatus 10 which integrates the function of determining the speed of sedimentation of blood and other parameters connected thereto, with the function of cell-counter, or other connected measurement.

The apparatus 10 comprises as its main components:

a pick-up member 11, of the needle type, able to selectively pick up a sample of blood to be analyzed from containers 22 housed in a storage drum 23, which can be made to rotate by a motor 21 in order to mix the blood;

a device to measure the ESR 14 comprising a capillary container 12, transparent to electromagnetic radiations in a field between 100 and 1500 nm, preferentially between 200 and 1000 nm, inside which the blood sample is able to be introduced;

a circuit 13 which connects the pick-up member 11 to the capillary 12 and inside which the blood sample is able to circulate;

an instant block pump 28 associated with the circuit 13;

an optical system associated with the capillary 12 and comprising at least a device 16 to emit electromagnetic radiations associated with a mating detector device 17, arranged on opposite sides with respect to a point of the capillary 12;

a measuring assembly 18, arranged in series with the capillary 12 and inside which the blood sample, after the speed of sedimentation has been measured, is able to circulate so that hematological measurements can be performed, such as counting the red cells, white cells, platelets, the hematocrit and other parameters relating to the form and size of the corpuscle part of the blood;

a discharge tank 19, where the blood sample which has been subjected to analysis is discharged and then disposed of;

a command and control unit 20 able to manage the functioning of the apparatus 10 and a plurality of interfaces, such as a monitor 24, keyboard 25 and printer 26, connected to the control unit 20 in order to set the functions of the apparatus 10, to display and print the results and possibly to connect on line in order to transmit and exchange information.

The command and control unit 20, by means of electric cables 27, governs and controls the functioning of the pick-up member 11, the stirrer motor 21, the block pump 28, a the optical system 16, 17 in order to determine the ESR, and the measuring assembly 18.

With the apparatus 10 as described above, a blood sample can be picked up, by means of the needle member 11, from one of the containers 22 arranged in the storage drum 23. The blood sample is sent, through the circuit 13 and the pump 28, inside the capillary 12 where, by means of the pump, it is instantaneously stopped in order to measure the ESR with the slopped-flow process described in EP'188.

Then, the flow is re-started by making the same blood sample (which has not undergone any chemical-physical alteration during the measurement of the ESR) pass without any break in continuity through the cell-counter measuring assembly 18, which performs the desired measurements, and from which the blood sample is then discharged into the tank 19.

In this way, the times to perform the desired measurements are reduced to a minimum, the quantity of blood to be used, and hence to be taken from the patient, can be greatly reduced, in the range of 30-200 µl, without needing to be diluted or have other reagents or anti-coagulants added. Moreover, the procedures to transfer the samples from one machine to the other are eliminated and hence the whole analysis is easier, quicker and more rational, also reducing the risks that additional handling might lead to exchanges and mistakes in identifying the sample.

The pump that makes the blood sample circulate in the circuit 13 can be arranged either upstream or downstream of the capillary 12 and, in a preferential embodiment, is of the reversible type and allows the blood to circulate in both directions.

According to a variant that is not shown here, the circulation circuit 13 is divided into two branches, a first passing through the device 14 to measure the ESR, and a second passing through the measuring assembly 18 which counts the cells.

The data acquired by the measuring devices 14 and 18 are transmitted in real time to the command and control unit 20 which memorizes them and processes them in order to obtain the ESR value, and correlated parameters, and also the count of the cells and the other values obtained in the measuring assembly 18. The data acquired can be compared or integrated with parameters present in a database inside the unit 20.

The results of the analysis can then be displayed on the display 24 and/or printed by the printer 26 while the blood sample is discharged into the tank 19. By obtaining the ESR values and, for example, the hematocrit simultaneously and with the same equipment, the analyst also has the advantage that he can make the desired comparisons and corrections according to the crossed parametric comparison of the respective values.

It is clear, however, that modifications and/or additions can be made to the apparatus 10 and method as described heretofore, without departing from the field and scope of the present invention.

For example, as we said, some components of the measuring assembly 18 can be upstream of the device 14 to detect the ESR. The instantaneous blockage of the flow of the blood sample along the circuit 13 can be performed by means of valve means associated with the circuit 13 and/or the capillary container 12.

The invention claimed is:

1. Integrated apparatus for hematological analyses, wherein it comprises, arranged substantially in line and integrated substantially in a single machine, an optical device to detect substantially instantaneously the speed of blood sedimentation (ESR) by measuring the optical density, or absorbance, of a blood sample, and a measuring assembly with a cell-counter function, said optical device for the detection of the ESR and said measuring assembly sharing a circuit for circulation of the same blood sample to be subjected first to the detection of the ESR and then to other measurements such as counting the red cells, white cells, platelets, the hematocrit and other parameters relating to the form and size of the corpuscle part of the blood, said optical device for the detection of the ESR and said measuring assembly with a cell-counter function sharing a pump associated on the circuit and for circulating the blood sample, said apparatus further including a single command and control unit controlling and governing the functioning of said optical device to detect the speed of blood sedimentation and said measuring assembly.

2. Integrated apparatus as in claim 1, wherein said optical device to detect the speed of blood sedimentation is arranged in series with said measuring assembly.

3. Integrated apparatus as in claim 1, further comprising a blood sample source, the blood sample source is common to both said optical device for the detection of the ESR and said measuring assembly with a cell-counter function, wherein said optical device for the detection of the ESR and said measuring assembly with a cell-counter function are both disposed downstream of the blood sample source.

4. Integrated apparatus as in claim 1, further comprising a collection element for one or more containers containing blood samples, associated with a pick-up member, said pick-up member being in fluid communication with said optical device so as to be able to make a sample of said blood circulate in close sequence and substantially without any break in continuity through a capillary tube of said optical device to detect the ESR and through said measuring assembly with cell-counter function.

5. Integrated apparatus as in claim 4, wherein said pick-up member includes a needle member, said one or more containers having a sealing top able to be perforated by said needle member.

6. Integrated apparatus as in claim 4, wherein said optical device includes means for instantaneously interrupting the blood flow (stopped flow) along said capillary tube.

7. Method to perform hematological analyses, wherein it provides that a blood sample, taken under control of a single command and control unit from a container by means of a pick-up needle member, is sent to and made to circulate in a single circuit which passes in close sequence, and substantially without any break in continuity, first through an optical device under control of the single command and control unit to detect substantially instantaneously the speed of blood sedimentation (ESR) by measuring the optical density, or absorbance, of the blood sample, and then through a measuring assembly under control of the single command and control unit to count the cells, or other measurement connected with counting cells, wherein said optical device and said measuring assembly are a single machine sharing a pump associated on the single circuit, and are arranged in line and without any break in continuity in order to be able to perform on the same blood sample first the measurement of the ESR and then other measurements such as counting the red cells, white cells, platelets, the hematocrit and other parameters relating to the form and size of the corpuscle part of the blood.

8. Method as in claim 7, wherein the speed of blood sedimentation is detected by means of an instantaneous stoppage of the flow of the blood sample passing in a capillary tube of said optical device, and by sending an optic beam through said capillary tube in order to detect the optical density at the point of stoppage of the blood inside the capillary tube, after which detection of the flow of blood is restarted for transit through said measuring assembly.

* * * * *